(12) United States Patent
Schillings et al.

(10) Patent No.: US 10,591,352 B2
(45) Date of Patent: Mar. 17, 2020

(54) SENSOR AND SYSTEM FOR PLANT CANOPY MEASUREMENT

(71) Applicant: X Development LLC, Mountain View, CA (US)

(72) Inventors: Benoit Schillings, Los Altos Hills, CA (US); Elliott Grant, Woodside, CA (US)

(73) Assignee: X Development LLC, Mountain View, CA (US)

( * ) Notice: Subject to any disclaimer, the term of this patent is extended or adjusted under 35 U.S.C. 154(b) by 212 days.

(21) Appl. No.: 15/867,158

(22) Filed: Jan. 10, 2018

(65) Prior Publication Data

US 2019/0212191 A1    Jul. 11, 2019

(51) Int. Cl.
| | |
|---|---|
| G01J 1/16 | (2006.01) |
| G01V 8/10 | (2006.01) |
| G01J 1/02 | (2006.01) |
| G01J 1/42 | (2006.01) |
| G01J 1/04 | (2006.01) |
| G01N 21/84 | (2006.01) |
| A01B 79/00 | (2006.01) |

(52) U.S. Cl.
CPC .......... *G01J 1/1626* (2013.01); *G01J 1/0219* (2013.01); *G01J 1/0228* (2013.01); *G01J 1/0247* (2013.01); *G01J 1/0271* (2013.01); *G01J 1/0488* (2013.01); *G01J 1/16* (2013.01); *G01J 1/4228* (2013.01); *G01N 21/84* (2013.01); *G01V 8/10* (2013.01); *A01B 79/005* (2013.01); *G01J 2001/1615* (2013.01); *G01J 2001/4266* (2013.01); *G01N 2021/8466* (2013.01)

(58) Field of Classification Search
CPC .... G01J 1/1626; G01J 1/16; G01J 2001/1615; G01V 8/10; A01B 79/005
USPC ...................................... 250/338.1
See application file for complete search history.

(56) References Cited

U.S. PATENT DOCUMENTS

| | | | |
|---|---|---|---|
| 8,451,449 B2 | 5/2013 | Holland | |
| 8,902,413 B2 | 12/2014 | Ulman et al. | |
| 9,674,458 B2 * | 6/2017 | Teich | .................... H04N 5/2354 |
| 9,848,113 B2 * | 12/2017 | Smits | ........................ G06T 7/90 |
| 10,082,576 B2 * | 9/2018 | Lee | ..................... H01L 27/1443 |
| 2005/0098713 A1 * | 5/2005 | Holland | .................... G01J 3/10 |
| | | | 250/221 |
| 2009/0234810 A1 * | 9/2009 | Angell | .................... G06Q 10/04 |
| 2010/0324830 A1 | 12/2010 | Solie et al. | |

(Continued)

OTHER PUBLICATIONS

Xue, J. et al., "Significant Remote Sensing Vegetation Indices: A Review of Developments and Applications", Hindawi Journal of Sensors, vol. 2017, Article ID 1353691, 2017, 17 pages.

*Primary Examiner* — Taeho Jo
(74) *Attorney, Agent, or Firm* — Christensen O'Connor Johnson Kindness PLLC

(57) ABSTRACT

A technique and apparatus for monitoring a plant canopy over a field is disclosed. The technique includes receiving first sensor values from a plurality of plant canopy sensors disposed in or on a ground of the field under the plant canopy. The first sensor values are indicative of near-infrared (IR) light reflected or reradiated from the plant canopy. Second sensor values are also received from the plant canopy sensors. The second sensor values are indicative of red light that is incident through the plant canopy. A map of the plant canopy may be generated based upon the first and second sensor values.

18 Claims, 8 Drawing Sheets

(56) References Cited

U.S. PATENT DOCUMENTS

| | | | | |
|---|---|---|---|---|
| 2011/0047867 A1* | 3/2011 | Holland | ................... | G01J 3/10 |
| | | | | 47/1.5 |
| 2013/0250280 A1* | 9/2013 | Holland | ................... | G01J 3/10 |
| | | | | 356/51 |
| 2015/0081058 A1* | 3/2015 | Oliver | ................... | A63F 13/245 |
| | | | | 700/91 |
| 2015/0090866 A1* | 4/2015 | Lee | ........................ | G01S 17/88 |
| | | | | 250/226 |
| 2015/0100168 A1* | 4/2015 | Oliver | ................... | A63F 13/245 |
| | | | | 700/284 |
| 2015/0379702 A1* | 12/2015 | Ulman | ................. | G06T 7/0002 |
| | | | | 348/207.1 |
| 2017/0030877 A1* | 2/2017 | Miresmailli | ............. | A01G 7/00 |
| 2018/0143130 A1* | 5/2018 | Shearer | ............... | A01B 79/005 |
| 2018/0278927 A1* | 9/2018 | Murata | .................... | G01J 1/16 |
| 2018/0284016 A1* | 10/2018 | Fujiyama | ............ | G01N 21/359 |
| 2019/0134508 A1* | 5/2019 | Matsuzawa | ............ | A63F 13/42 |
| 2019/0162885 A1* | 5/2019 | Nash | ........................ | G02B 5/28 |

\* cited by examiner

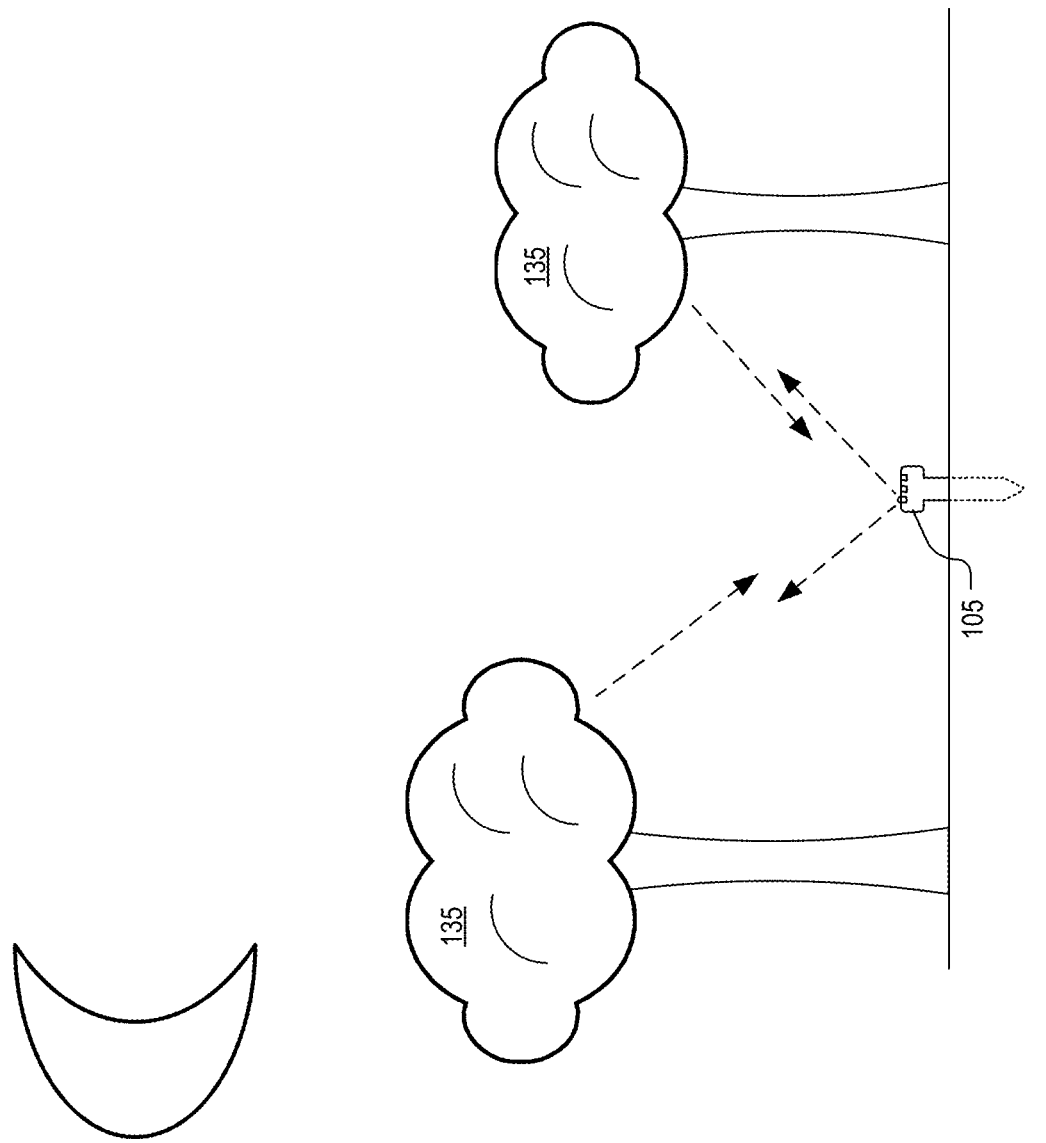

SENSOR AND SYSTEM FOR PLANT CANOPY MEASUREMENT

TECHNICAL FIELD

This disclosure relates generally to sensor systems, and in particular but not exclusively, relates to sensors for precision agriculture.

BACKGROUND INFORMATION

Precision agriculture is a plant management technique that uses observations and measurements to identify and respond to intra-field variability of vegetation. Conventionally, visually based observations are often from aerial or satellite photography that generate vegetation maps, hopefully with reasonable latency to provide up-to-date feedback. One such visual based observation is a normalized difference vegetation index (NDVI) imaging, which is often used to generate NDVI maps. NDVI maps have been found to successfully identify live vegetation.

Live green plants absorb solar radiation in the photosynthetically active radiation spectrum (e.g., the "red edge" around 700 nm) to support photosynthesis. Correspondingly, the structure of vegetation also tends to reflect near-infrared light since absorbing this spectrum would cause a plant to overheat. Accordingly, live green vegetation tends to image dark at the red edge around 700 nm while imaging bright in the near-IR band. The NDVI uses a ratio of near infrared (IR) light to red edge light to generate images that distinguish vegetation from non-vegetation. However, these images have conventionally been acquired from above using expensive aerial or satellite photography.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 3D illustrates operation of a plant canopy sensor using an on-board illuminator to illuminate an underside of a plant canopy with red light and near-infrared light, in accordance with an embodiment of the disclosure.

DETAILED DESCRIPTION

Figure 1:
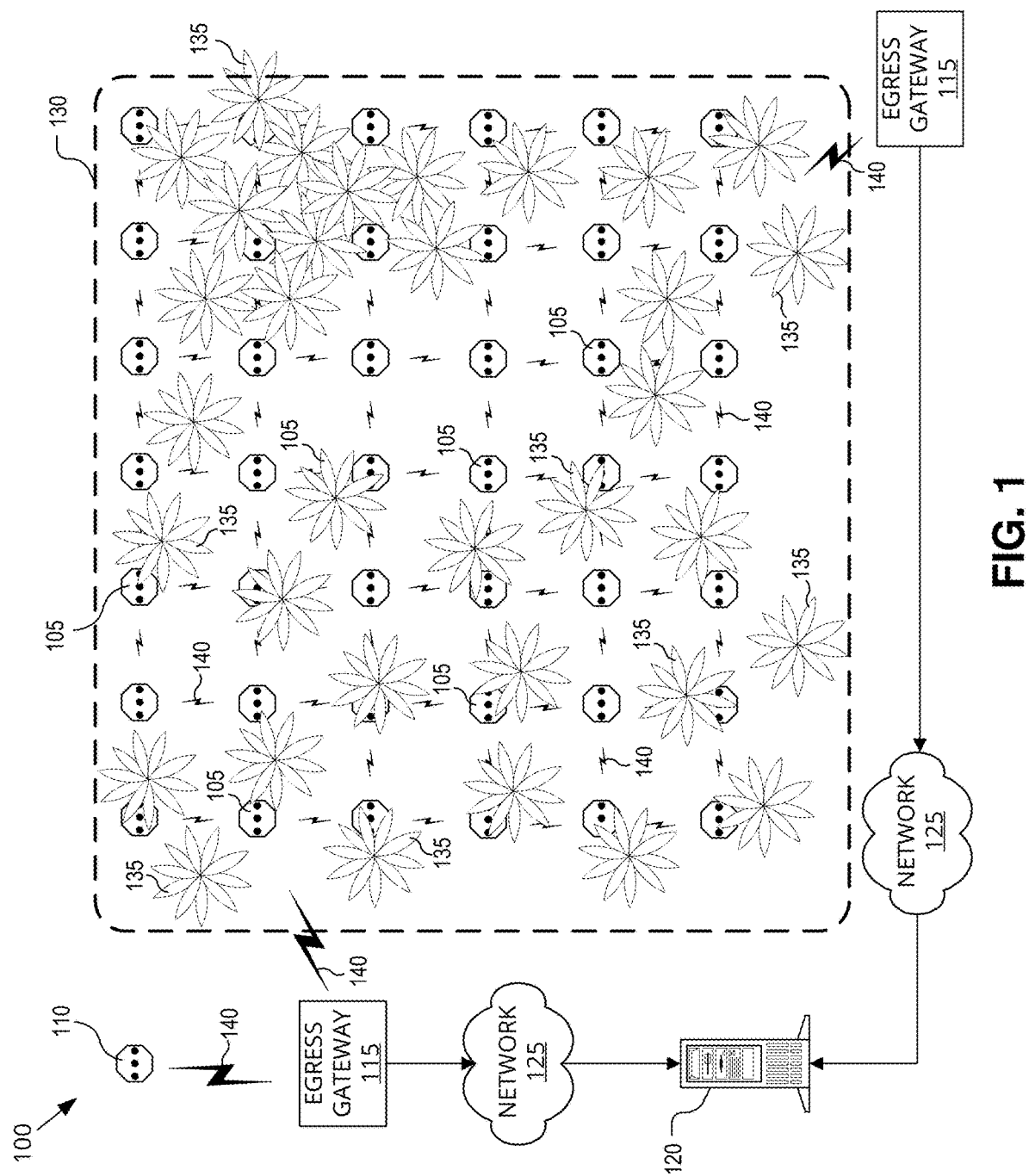
FIG. 1 is an illustration of a plant canopy monitoring system, in accordance with an embodiment of the disclosure.

Embodiments of a system, apparatus, and method for monitoring changes in a plant canopy over a field are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Conventional plant canopy imaging techniques use a normalized difference vegetation index (NDVI), or other vegetation indexes, generated from a top down approach of aerial or satellite photography where the images are taken of the topside of the plant canopy. Aerial and satellite photography is relatively expensive, may not have the level resolution desired, and can have delays associated with acquiring and distributing the information to the end user. Embodiments described herein implement a bottom up approach that uses a plurality of ground based sensors that image the bottom side of the plant canopy over a field to monitor and track the growth or health of plants in the field. The plant canopy may be leaves of tall trees, leaves of low lying shrubs (e.g., strawberry bushes), or anything in between that photosynthesizes. Since this bottom up approach is ground based, these sensors can be networked using wireless technologies to provide near real-time or regular, periodic feedback to the end user. Since these ground based sensors are so much closer to the plant canopy, relative to aerial and satellite photography, these sensors do not require sophisticated optics or expensive image sensor arrays. Accordingly, embodiments described herein may use low cost sensors that are randomly or evenly distributed across the field beneath the plant canopy to image the bottom side of the plant canopy using a bottom up NDVI. This imaging data, in the form of sensor values, can be communicated over wireless and ground base networks to a remote server for near real-time data analysis.

The low cost and easy deployment nature of the system and apparatuses described herein are well suited for precision agriculture. The feedback data provided to a farmer can be highly accurate with low latency and provide automated crop analysis at a relative granular level. The data analysis of the bottom up NDVI sensor values may be correlated to growth, health, disease, or other conditions of the plants growing (or not growing) in the field. The near real-time data may provide detailed up-to-date maps of a field, may be thresholded for alarm conditions, may be tracked over time for historical analysis, or otherwise.

FIG. 1 is an illustration of a plant canopy monitoring system 100, in accordance with an embodiment of the disclosure. The illustrated embodiment of system 100 includes plant canopy sensors 105 and 110, one or more egress gateways 115, and a server 120 communicatively coupled to plant canopy sensors 105 and 110 via one or more networks 125 and wireless mesh network 140. Plant canopy sensors 105 are positioned throughout a field 130 on the ground beneath a plant canopy 135. Plant canopy 135 extends across field 130 and includes dense sections and sparse sections having various gaps dispersed throughout. On the other hand, plant canopy sensor 110 is positioned in an open location having an unobstructed view of the sky above field 130. Plant canopy sensors 105 are operated to measure plant canopy 135 within field 130 and as such, may be referred to herein as "field sensors." Correspondingly, plant canopy sensor 110 is operated to acquire reference data of solar illumination for optionally normalizing the sensor data obtained from the field sensors. As such, plant canopy sensor 110 may be referred to herein as a "reference sensor."

In the illustrated embodiment, plant canopy sensors 105 and 110 each include wireless transceivers and intercommunicate over distributed wireless mesh network 140. In one embodiment, mesh network 140 enables each plant canopy sensor 105 or 110 to operate as a network node that connects in a non-hierarchical manner to as many other nodes as possible with each networking node cooperating to route data across mesh network 140 to one or more egress gateways 115. In one embodiment, mesh network is a 900 MHz, frequency hopping grid distribution network. Of course, other frequency, distribution, or networking protocols may be used. Mesh network 140 enables plant canopy sensors 105 and 110 to be distributed over a large area, such as field 130 while having only one (or more) peripherally located egress gateways 115. Egress gateways 115 provide extraction points for exporting the sensor data from mesh network 140 onto network 125 (e.g., the Internet, a LAN, a WAN, a MAN, etc.) for ultimate delivery to remotely located server 120.

Figure 2:
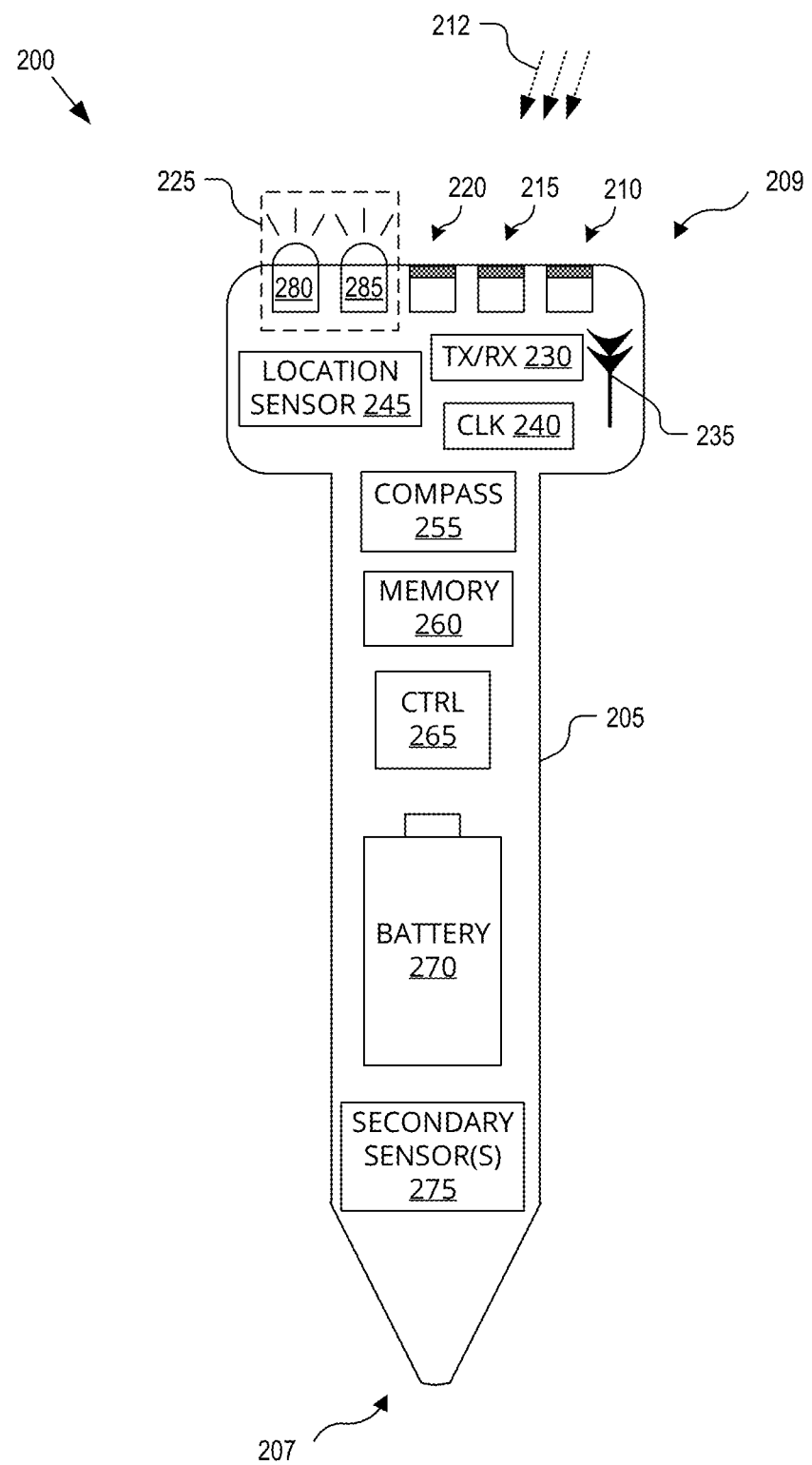
FIG. 2 is a functional block diagram of a plant canopy sensor, in accordance with an embodiment of the disclosure.

FIG. 2 is a functional block diagram of a plant canopy sensor 200, in accordance with an embodiment of the disclosure. The illustrated embodiment of plant canopy sensor 200 is one possible implementation of plant canopy sensors 105 or 110. The illustrated embodiment of plant canopy sensor 200 includes a housing 205, a near-infrared (IR) photo-sensor 210, a red photo-sensor 215, a broadband photo-sensor 220, an on-board illuminator 225, transceiver circuitry 230, an antenna 235, a clock 240, a location sensor 245, a compass 255, memory 260, a controller 265, a battery(ies) 270, and secondary sensor(s) 275. The illustrated embodiment of on-board illuminator 225 includes a near-IR emitter 280 and a red light emitter 285. It should be appreciated that various implementations of plant canopy sensor 200 may omit one or more of the components illustrated in FIG. 2. For example, in one embodiment, on-board illuminator 225, compass 255, and secondary sensors 275 are omitted.

The illustrated embodiment of housing 205 includes a first end 207 having a shape to be placed on, or inserted into, the ground beneath plant canopy 135. Housing 205 also includes a second end 209, opposite end 207, which provides a mounting location from which photo-sensors 210, 215, and 220 can image the plant canopy 135 above.

Near-IR photo-sensor 210 is oriented to be sensitive to near-IR light reflected or reradiated from plant canopy 135, when plant canopy sensor 200 is positioned beneath plant canopy 135. Red photo-sensor 215 is oriented to be sensitive to red light that encourages photosynthesis which is incident from plant canopy 135 when plant canopy sensor 200 is positioned beneath plant canopy 135. Broadband photo-sensor 220 is oriented to be sensitive to solar light incident from above the ground. Broadband photo-sensor 220 is configured to measure broadband visible spectrum solar illumination.

The sensor values output from near-IR photo-sensor 210 and red photo-sensor 215 may be used in a ratio to calculate an NDVI, or other ratio of wavelengths, for the particular point location where plant canopy sensor 200 is positioned. When a plurality of vegetation indexes are calculated from many point locations corresponding to each plant canopy sensor 105 (FIG. 1) in field 130, a vegetation index map (e.g., NDVI index map) of plant canopy 135 may be generated. In one embodiment, the sensor values output from broadband photo-sensor 220 provides a general solar brightness measure. In addition to being a general solar brightness measure, the sensor values output from broadband photo-sensor 220 may also be used to normalize or otherwise offset/adjust the sensor values output from near-IR photo-sensor 210 and red photo-sensor 215. In addition, the sensor values acquired from reference sensor 110 (FIG. 1) may also (or alternatively) be used as the general solar brightness measure and/or for normalizing the sensor values acquired from field sensors 105 when acquired in a contemporaneous, or approximately contemporaneous (e.g., within 15 or 30 mins), period.

In one embodiment, near-IR photo-sensor 210, red photo-sensor 215, broadband photo-sensor 220 are implemented as single pixel photo-sensors that each have a different bandpass response to incident light 212. In one embodiment, near-IR photo-sensor 210 is overlaid with a near-IR bandpass filter having a bandpass that falls between approximately 800 nm and approximately 1000 nm. In one embodiment, red photo-sensor 215 is overlaid with a red light bandpass filter having a bandpass that falls between approximately 680 nm and 720 nm. In one embodiment, broadband photo-sensor 220 is overlaid with a visible spectrum bandpass filter having a bandpass that falls between approximately 400 nm and approximately 600 nm. Of course, the bandpass filters covering photo-sensors 210 and 215 may be implemented with different bandpasses covering different combinations of wavelength ranges to generate a variety of different vegetation indexes of interest. Furthermore, photo-sensors 201, 215, and 220 may be implemented using a variety of different technologies such as photodiodes, photo-resistors, solar cells, a charge coupled device sensor, a complementary metal-oxide-semiconductor sensor, or otherwise. The bandpass filters may be absorptive or reflective (e.g., diffraction grating). Alternatively, the bandpass filters may be incorporated into the design of each photo-sensor as opposed to being an overlaying element.

Location sensor 245 may be included with plant canopy sensor 200 to measure a physical location (e.g., coordinate location) of plant canopy sensor 200. Location sensor 245 may be implemented as a global positioning sensor (GPS), a triangulation sensor, or otherwise. Location sensor 245 may be used to establish a coordinate location for each plant canopy sensor 105 for recreating a map of plant canopy 135 over field 130.

Compass 255 may be included with plant canopy sensor 200 to measure a directional orientation of plant canopy sensor 200 when deployed in field 130. Compass 255 may be implemented using a variety of technologies such as a solid state compass, a GPS receiver compass, a gyrocompass, a magnetic compass, or otherwise.

Secondary sensor(s) 275 may also be optionally included within housing 205 to gather other forms of data about the environment of field 130. For example, secondary sensor(s) 275 may include one or more of an air humidity sensor, a soil ph sensor, a soil moisture sensor, a rain gauge, a ground or air thermometer, or otherwise.

In the illustrated embodiment, on-board illuminator 225 is disposed at the second end 209 to provide on-demand or periodic illumination of the underside of plant canopy 135. In one embodiment, a near-IR emitter 280 is configured to emit near-IR light (e.g., between 800 nm and 1000 nm) while red light emitter 285 is configured to emit red edge light (e.g., red light between 680 nm to 720 nm). In yet another embodiment, on-board illuminator 225 may include a single light source that emits red light and near-IR light.

Controller 265 is a microcontroller coupled to the other functional components of plant canopy sensor 200 to control and choreograph their operations. Controller 265 may be implemented using hardware logic (e.g., application specific integrated circuit, field programmable gate array, etc.), implemented as a microprocessor that executes software/firmware stored in memory 260, or a combination of both. Memory 260 may include non-volatile memory (e.g., flash memory) and/or volatile memory. Controller 265 is further coupled to acquire sensor values from photo-sensors 210, 215, 220, and/or secondary sensors 275 and wirelessly transmit them over mesh network 140 via transceiver 230 (e.g., a transmitter and/or receiver) and antenna 235. In one embodiment, controller 265 periodically reads sensors values from photo-sensors 210, 215, 220, and/or secondary sensors 275, stores them in memory 260 indexed to time, date, and/or location, and then periodically transmits them to server 120.

In the illustrated embodiment, battery 270 (or batteries) is included within housing 205 to power the other on-board components. Battery 270 may be a rechargeable or non-rechargeable battery (e.g., two AAA batteries).

Figure 3A:
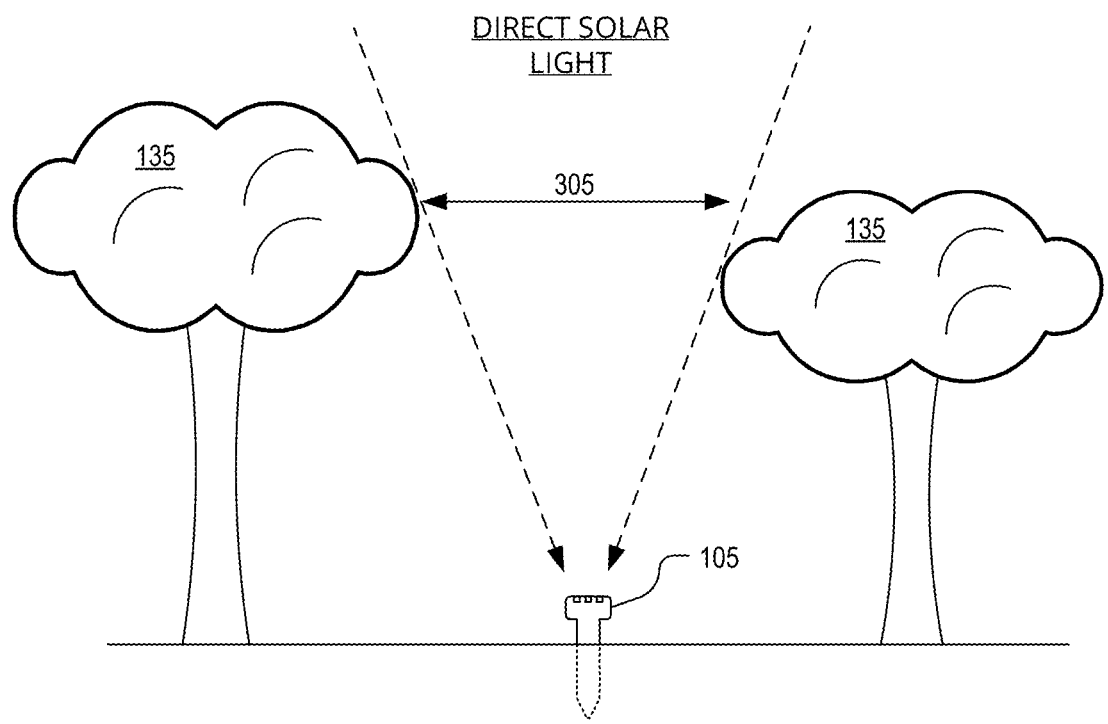
FIG. 3A illustrates operation of a plant canopy sensor when measuring direct solar light through gaps in a plant canopy, in accordance with an embodiment of the disclosure.

FIGS. 3A-3D illustrate operation of a plant canopy sensor 105 when optically measuring the underside of plant canopy 135 using photo-sensors 210, 215, and 220. In particular, FIG. 3A illustrates how photo-sensors 210, 215, and 220 of a field sensor 105 can be used to measuring near-IR light, red light, and broadband visible light, respectively, that is direct solar radiation through gaps or openings 305 in plant canopy 135. The sensor values, or ratio of the sensor values acquired by photo-sensors 210, 215, and 220, may be analyzed to identify and distinguish direct solar radiation.

Figure 3B:
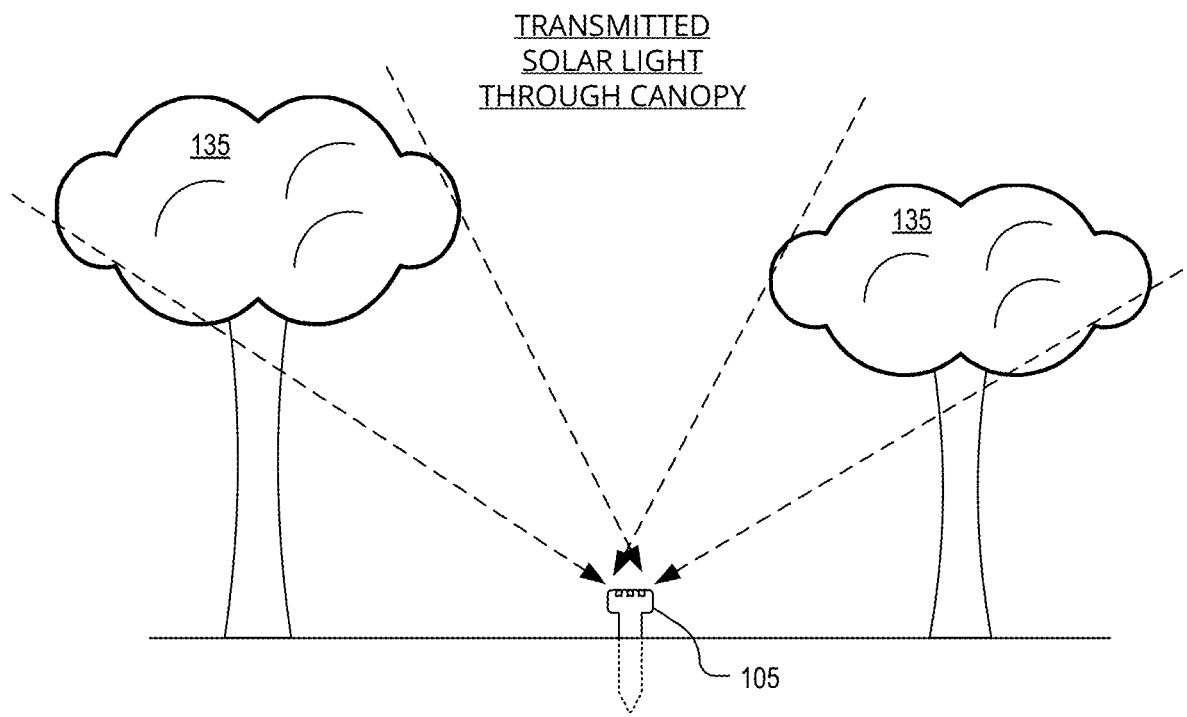
FIG. 3B illustrates operation of a plant canopy sensor when measuring solar light transmitted through a plant canopy, in accordance with an embodiment of the disclosure.

In contrast, FIG. 3B illustrates how photo-sensors 210, 215, and 220 of a field sensor 105 can be used to measuring near-IR light, red light, and broadband visible light, respectively, that is transmitted through plant canopy 135. Since the chlorophyll in live photosynthesizing plant canopies absorbs red light, this absorption can be identified in the ratio of near-IR and red light of an NDVI calculation. Accordingly, light transmitted through a live plant canopy can be identified from appropriate analysis. Correspondingly, live or dead plants tend to reflect and/or absorb and reradiate near-IR light. This interaction difference of plant canopy 135 to near-IR light and red light can also be leveraged to identify light that passes through the plant canopy 135.

Figure 3C:
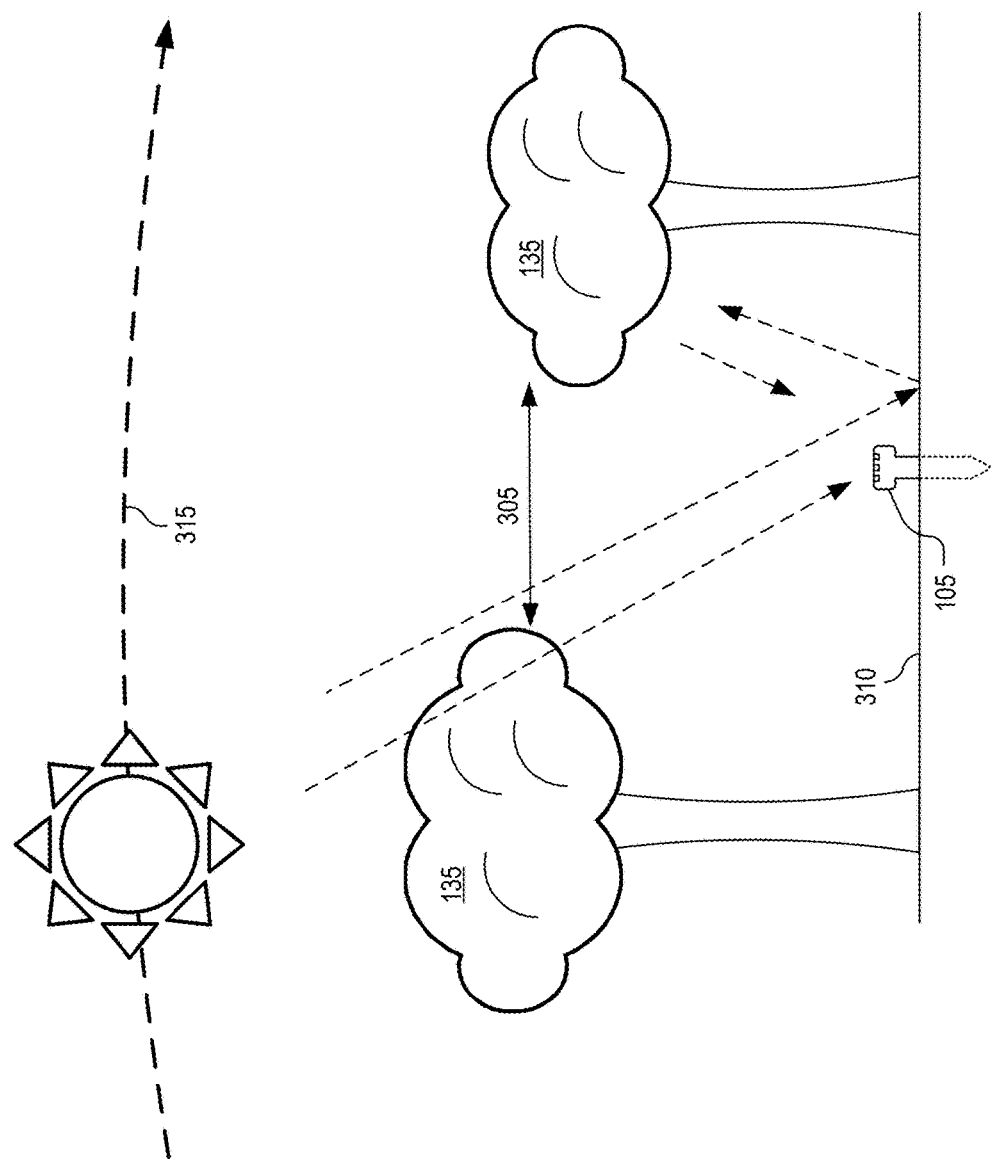
FIG. 3C illustrates operation of a plant canopy sensor when measuring reflected solar light that passes through gaps in a plant canopy, in accordance with an embodiment of the disclosure.

FIG. 3C illustrates how direct light that passes through canopy gap 305 reflects off the ground 310, and is then reflected or absorbed and reradiated from the underside of plant canopy 135 towards field sensor 105. This configuration may also leveraged the difference of absorption and reflection between red light and near-IR light to identify the presence or absence of plant canopy 135 above a given field sensor 105. Additionally, FIG. 3C illustrates how the sun path 315 may also be leveraged to map plant canopy 135 with greater resolution. The shadows cast on field sensor 105 will change over the course of a day and are related to the direction and declination of the sun at any given time. The direction and declination of the sun with respect to field 130 may be determined based upon the geographic location, date, and time, which are values that may be indexed to each sensor value by field sensor 105 and/or server 120. The sun path data may be referenced to increase the resolution of a map generated using the sensor values from field sensors 105 deployed throughout field 130.

Finally, FIG. 3D illustrates an embodiment where on-board illuminator 225 is activated under the influence of controller 265 to illuminate the underside of plant canopy 135. By analyzing the ratios between the sensor values acquired by photo-sensors 210, 215, and 220, the presence or absence of live or dead plant canopy 135 may also be determined.

Figure 4:
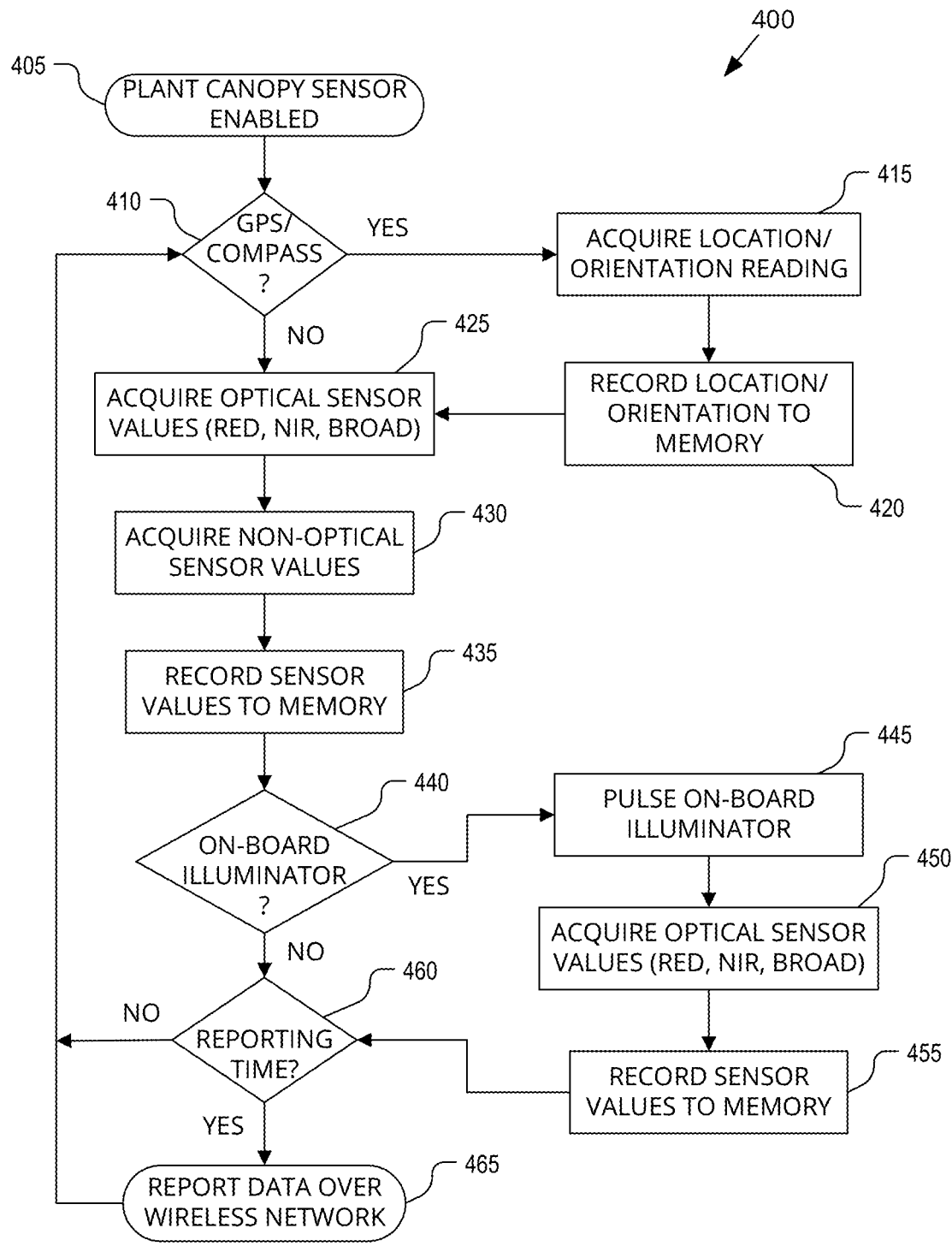
FIG. 4 is a flow chart illustrating a process of operation of a plant canopy sensor, in accordance with an embodiment of the disclosure.

FIG. 4 is a flow chart illustrating a process 400 of operation of plant canopy sensor 200, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, plant canopy sensor 200 is enabled. Enablement may occur when power is applied, when secondary sensors 275 sense that plant canopy sensor 200 has been placed into or onto soil, or when otherwise enabled (locally or remotely).

In a decision block 410, if the particular embodiment of plant canopy sensor 200 includes a location sensor 245 or a compass 255, process 400 continues to process block 415 where a location and/or directional orientation of plant canopy sensor 200 is measured. In a process block 420, the location and/or orientation data is recorded into memory 260.

In a process block 425, controller 265 acquires sensor values from near-IR photo-sensor 210, red photo-sensor 215, and optionally broadband photo-sensor 220. Non-optical sensor values may be optionally read from secondary sensors 275 in a process block 430. The sensor values are then recorded into memory 260. In some embodiments, the sensor values are indexed to one or more of date, time, location or directional orientation by controller 265.

In a decision block 440, if plant canopy sensor 200 includes on-board illuminator 225, then process 200 continues to a process block 445. Controller 265 pulses on-board illuminator 225 (process block 445), acquires sensor values from photo-sensors 210, 215, and 220, as a result of pulsing on-board illuminator 225 (process block 450), and records the sensor values into memory 260 (process block 455). In one embodiment, the sensor values acquired using artificial illumination from on-board illuminator 225 are also index with an indication that they were acquired using on-board illuminator 225.

If controller 265 is not yet ready to report the accumulated sensor values (decision block 460), then controller 265 continues to accumulate sensor values until it is time to report the sensor values to server 120 over mesh network 140 (process block 465). Sensor values may be acquired periodically, continuously, on-demand, upon receive of a remote request from server 120, or otherwise. Reporting of the sensor values to server 120 may be immediate, periodic, polled by server 120, pushed by controller 265 to server 120, transmitted when bandwidth permits, or otherwise. It should be appreciated that depending upon the configuration of plant canopy sensor 105, optical sensor values may be acquired during daytime at process block 425 based upon solar radiation while sensor values may also (or alternatively) be acquired during nighttime at process block 450 based upon artificial illumination from on-board illuminator 445. Both illumination regimes (natural vs artificial) may be used, or just one of the illumination regimes may be used.

Figure 5:
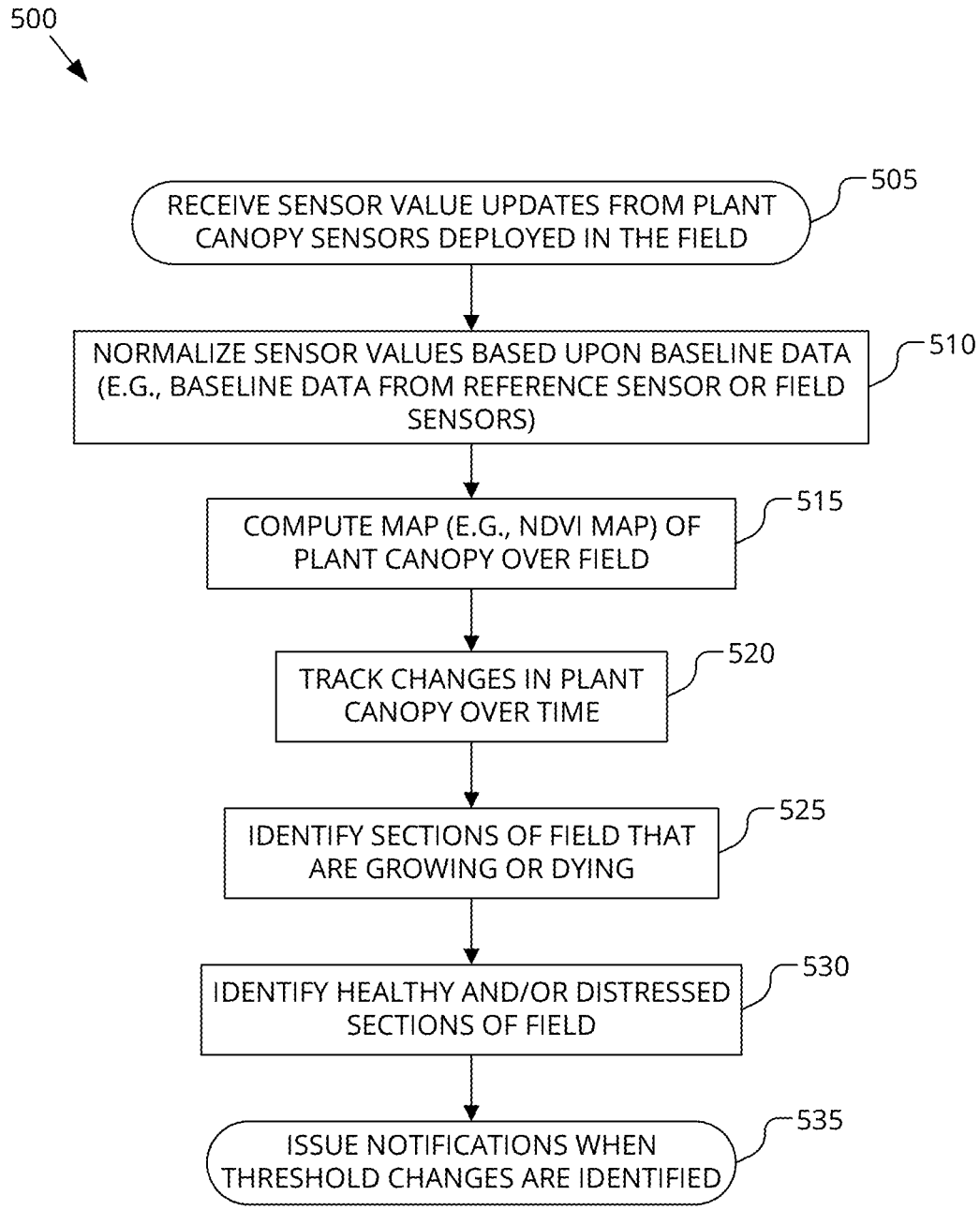
FIG. 5 is a flow chart illustrating a process of operation of a plant canopy monitoring server, in accordance with an embodiment of the disclosure.

FIG. 5 is a flow chart illustrating a process 500 of operation of plant canopy monitoring server 120, in accordance with an embodiment of the disclosure. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel.

In a process block 505, server 120 receives sensor data updates (e.g., optical sensor values and/or non-optical sensor values) from plant canopy sensors 105 deployed in field 130. The sensor values may be received already indexed to location, date, and time, or server 120 may use existing knowledge of the location of field 130 and the date/time of receipt of the sensor values to perform its own indexing.

In process block 510, the sensor values are normalized based upon baseline data also received from the plant canopy sensors 105 or 110. For example, the broadband solar illumination values (reference sensor values) received from reference sensor 110 may be used to offset or otherwise normalize the sensor values from photo-sensors 210, 215, and 220 within field sensors 105. For example, differences in received intensity values between reference sensor 110 and field sensors 105 may be used to compute a percent plant canopy coverage or occlusion at each field sensor location. The reference sensor values may be considered to represent a broadband visible spectrum measurement of solar illumination at the time of their acquisition (e.g., was it sunny or cloudy when the data was acquired). Alternatively (or additionally), the broadband sensor values acquired by broadband photo-sensors 220 within the field sensors 105 themselves may also be used to normalize or smooth the sensor values received from near-IR photo-sensors 210 and red photo-sensors 215. It should be appreciated that normalization of the data may be optional.

Figure 6:
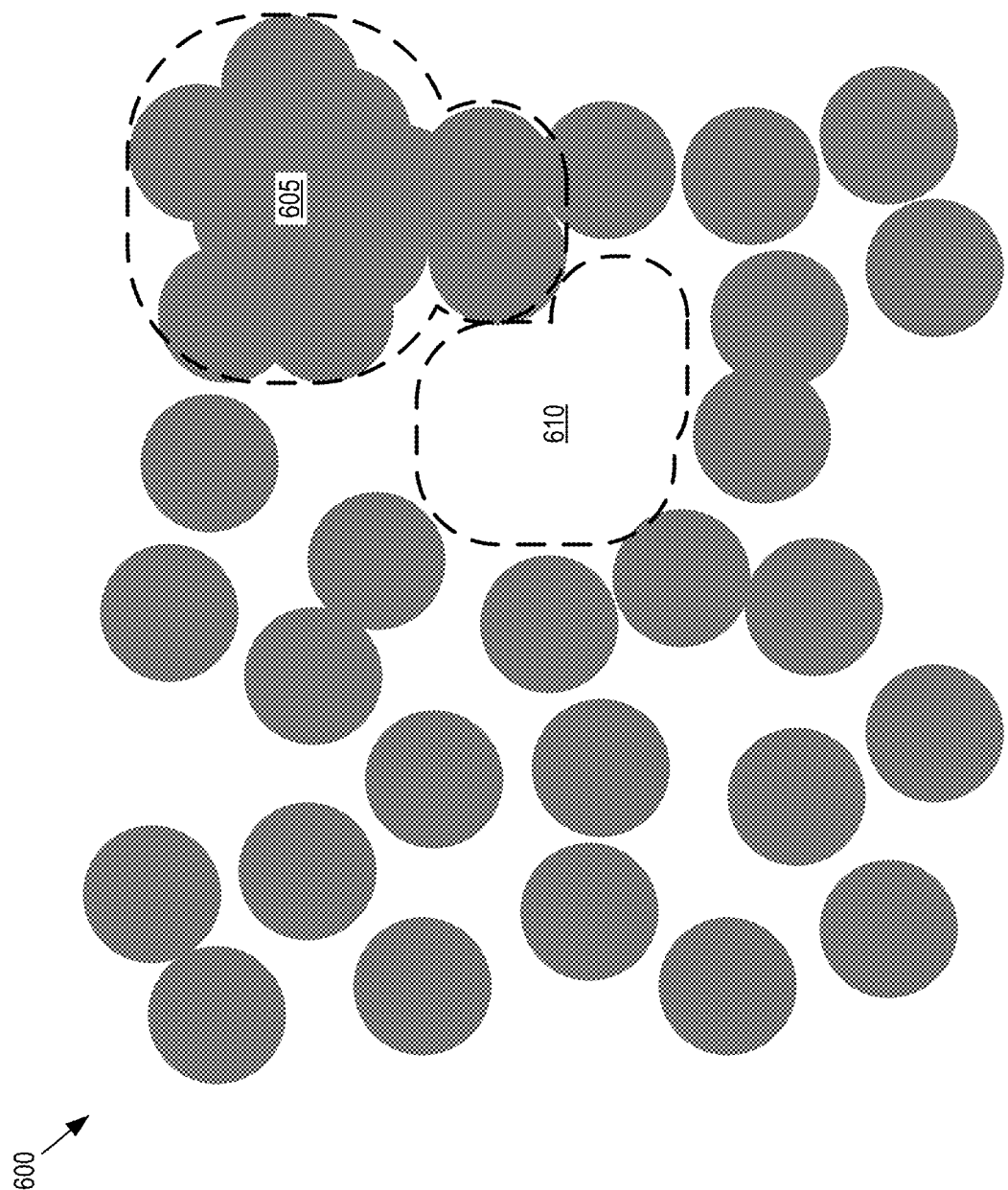
FIG. 6 illustrates an example vegetation index map of a plant canopy using sensor data acquired by a plurality of plant canopy sensors deployed in a field beneath the plant canopy, in accordance with an embodiment of the disclosure.

In a process block 515, the received sensor values are analyzed to compute a map or contour of plant canopy 135 over field 130. In one embodiment, the maps are generated based upon a statistical analysis of the sensor values. In yet another embodiment, machine learning algorithms are used to analyze the sensor values. In one embodiment, at least a vegetation index map (e.g., NDVI map) is generated. FIG. 6 illustrates an example NDVI map 600 of plant canopy 135. Of course, other types of vegetation indexes (e.g., Ratio Vegetation Index, Difference Vegetation Index, Green Vegetation Index, Perpendicular Vegetation Index, etc.) may also be used to generate a map of plant canopy 135. With regularly acquired sensor values, changes in the crop or plants growing in field 130 can be tracked over time (process block 520). Various growth, health, or distress conditions throughout field 130 can be inferred from changes in plant canopy 135 as determined from NDVI map 600. For example, growing sections or dying sections of a crop can be identified based upon changes in NDVI map 600 (process block 525). Correspondingly, healthy or distressed sections of field 130 may also be inferred. For example, section 605 may be deemed a healthy section of field 130 while section 610 may be identified as a distressed or dying section. Rates of change or absolute canopy coverage percentages may be values that are thresholded for issuing automated alarms to a user (process block 535). Additionally, the sensor values may be accumulated over many seasons to provide historical analysis and archival reference.

The processes explained above may be described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A sensor apparatus, comprising:
   a housing having a first end shaped for placing on, or inserting into, a ground;
   a first photo-sensor disposed at a second end, opposite the first end, of the housing and having a near-infrared (IR) bandpass filter, the first photo-sensor oriented to be sensitive to near-IR light received from above the sensor opposite the first end;
   a second photo-sensor disposed at the second end of the housing and having a red light bandpass filter, the second photo-sensor oriented to be sensitive to red light received from above the sensor opposite the first end;
   a third photo-sensor disposed at the second end of the housing, the third photo-sensor oriented to be sensitive to solar light incident from above the ground when the first end of the housing is placed in or on the ground, wherein the third photo-sensor is configured and oriented to measure broadband visible spectrum solar illumination for normalizing sensor values from the first and second photo-sensors;

a wireless transmitter disposed within the housing; and a controller coupled to the first, second, and third sensors to acquire the sensor values from the first, second, and third photo-sensors and coupled to the wireless transmitter to wirelessly transmit the sensor values via the wireless transmitter, wherein the sensor apparatus comprises a plant canopy sensor and the first, second, and third photo-sensors are orientated on the housing for collectively mapping a shape or tracking changes in the shape of a plant canopy from below the plant canopy.

2. The sensor apparatus of claim 1, wherein the first photo-sensor is oriented to be sensitive to the near-IR light reflected or reradiated from a plant canopy when the first end of the housing is placed in or on the ground beneath the plant canopy, and wherein the second photo-sensor is oriented to be sensitive to the red light that encourages photosynthesis which is incident from the plant canopy when the first end of the housing is placed in or on the ground beneath the plant canopy.

3. The sensor apparatus of claim 1, further comprising memory disposed within the housing and coupled to the controller, wherein the controller includes logic that when executed by the controller causes the sensor apparatus to perform operations including:

periodically acquiring the sensor values;

storing the sensor values into the memory indexed to time of acquisition; and periodically transmitting the sensor values via the wireless transmitter to a remote server.

4. The sensor apparatus of claim 1, further comprising:

a location sensor disposed in or on the housing and coupled to the controller, the location sensor for determining a location of the sensor apparatus, wherein the controller is configured to transmit the location via the wireless transmitter.

5. The sensor apparatus of claim 1, wherein the wireless transmitter is configured for communicating over a mesh network established by a plurality of instances of the sensor apparatus.

6. The sensor apparatus of claim 1, wherein:

the near-IR bandpass filter has a first bandpass that falls between approximately 800 nm and approximately 1000 nm, the red light bandpass filter has a second bandpass that falls between approximately 680 nm and approximately 720 nm, and the third photo-sensor includes a visible spectrum bandpass filter having a third bandpass that falls between approximately 400 nm and approximately 600 nm.

7. The sensor apparatus of claim 1, further comprising:

a compass disposed in or on the housing for determining a directional orientation of the sensor apparatus when placed on, or inserted into, the ground, wherein the controller is coupled to the compass to transmit the directional orientation of the sensor apparatus via the wireless transmitter.

8. The sensor apparatus of claim 1, further comprising:

an on-board illuminator disposed in or on the housing at the first end to illuminate an underside of a plant canopy, the on-board illuminator configured to emit the near-IR light and the red light.

9. The sensor apparatus of claim 8, wherein the controller includes logic that when executed by the controller causes the sensor apparatus to perform operations including:

transmitting an indication via the wireless transmitter of whether the sensor values were acquired using the on-board illuminator.

10. A method of monitoring changes in a plant canopy over a field, the method comprising:

receiving first sensor values from a plurality of plant canopy sensors disposed in or on a ground of the field under the plant canopy, the first sensor values indicative of near-infrared (IR) light reflected or reradiated from the plant canopy;

receiving second sensor values from the plant canopy sensors, the second sensor values indicative of red light, which encourages photosynthesis, that is incident through the plant canopy;

acquiring reference sensor values from a reference sensor positioned in or adjacent to the field at an open location having an unobstructed view of a sky above the field, wherein the reference sensor values represent a broadband visible spectrum measurement of solar illumination;

normalizing the first and second sensor values based upon the reference sensor values acquired approximately contemporaneously with the first and second sensor values; and generating a map of the plant canopy based upon the first and second sensor values.

11. The method of claim 10, further comprising:

tracking changes in the plant canopy over time; and identifying healthy or distressed areas of the field based upon the changes in the plant canopy.

12. The method of claim 11, further comprising:

issuing a notification when a threshold change in the plant canopy tracked over time indicates a plant distress condition; and indicating on the map where in the field the plant distress condition is occurring.

13. The method of claim 10, wherein the first and second sensor values are indexed to dates and times of when the first and second sensor values were acquired by the plant canopy sensors and indexed to a field location of the plant canopy sensors, and wherein generating the map of the plant canopy comprises:

identifying sun path data based upon the dates and the field location of the plant canopy sensors, wherein the sun path data changes based upon the field location and a time of year; and referencing the sun path data to increase a resolution of the map calculated based upon the sensor values.

14. The method of claim 10, wherein receiving the first and second sensor values includes receiving the first and second sensor values from a wireless mesh network that communicatively interconnects the plant canopy sensors to an egress gateway.

15. The method of claim 10, further comprising:

acquiring third sensor values indicative of broadband visible spectrum solar illumination incident through the plant canopy with the plant canopy sensors; and transmitting the third sensor values over the wireless mesh network to the remote server for monitoring changes in the plant canopy over time.

16. The method of claim 15, further comprising:

analyzing the first, second, and third sensor values with a machine learning algorithm to identify one or more of a growing status, a dying status, a health status, or a distress status of plants within the field.

17. A machine-accessible storage medium that provides instructions that, when executed by a machine, will cause the machine to perform operations for monitoring changes in a plant canopy over a field, the operations comprising:

receiving first sensor values from a plurality of plant canopy sensors disposed in or on a ground of the field under the plant canopy, the first sensor values indicative of near-infrared (IR) light reflected or reradiated from the plant canopy;

receiving second sensor values from the plant canopy sensors, the second sensor values indicative of red light, which encourages photosynthesis, that is incident through the plant canopy;

indexing the first and second sensor values to dates and times of when the first and second sensor values were acquired by the plant canopy sensors;

associating the first and second sensor values to a field location of the plant canopy sensors; and generating a map of the plant canopy based upon the first and second sensor values, wherein generating the map of the plant canopy comprises:

identifying sun path data based upon the dates and the field location of the plant canopy sensors, wherein the sun path data changes based upon the field location and a time of year; and referencing the sun path data to increase a resolution of the map calculated based upon the sensor values.

18. A machine-accessible storage medium that provides instructions that, when executed by a machine, will cause the machine to perform operations for monitoring changes in a plant canopy over a field, the operations comprising:

receiving first sensor values from a plurality of plant canopy sensors disposed in or on a ground of the field under the plant canopy, the first sensor values indicative of near-infrared (IR) light reflected or reradiated from the plant canopy;

receiving second sensor values from the plant canopy sensors, the second sensor values indicative of red light, which encourages photosynthesis, that is incident through the plant canopy;

acquiring reference sensor values from a reference sensor, wherein the reference sensor values represent a broadband visible spectrum measurement of solar illumination;

normalizing the first and second sensor values based upon the reference sensor values acquired approximately contemporaneously with the first and second sensor values; and generating a map of the plant canopy based upon the first and second sensor values.

* * * * *